United States Patent [19]

Finney

[11] 4,381,767

[45] May 3, 1983

[54] PENILE IMPLANT

[75] Inventor: Roy P. Finney, Tampa, Fla.

[73] Assignee: Medical Engineering Corporation, Racine, Wis.

[21] Appl. No.: 169,174

[22] Filed: Jul. 15, 1980

[51] Int. Cl.³ .............................................. A61F 5/00
[52] U.S. Cl. ..................................... 128/79; 128/1 R
[58] Field of Search ................. 128/1 R, 79, DIG. 25, 128/341, 295; 3/1.5

[56] References Cited

U.S. PATENT DOCUMENTS

| | | | |
|---|---|---|---|
| 2,085,368 | 6/1937 | Kendall | 128/341 |
| 3,171,409 | 3/1965 | Cetrone | 128/99 |
| 3,565,073 | 2/1971 | Tatooles et al. | 128/283 |
| 3,628,535 | 12/1971 | Ostrowski | 3/1.5 X |
| 3,835,857 | 9/1974 | Rogers et al. | 128/295 |
| 3,863,638 | 2/1975 | Rogers et al. | 128/295 |
| 3,991,752 | 11/1976 | Gerow | 128/79 |
| 4,187,851 | 2/1980 | Hauser | 128/295 |
| 4,209,009 | 6/1980 | Hennig | 128/DIG. 25 X |

FOREIGN PATENT DOCUMENTS 2652353 2/1978 Fed. Rep. of Germany ........ 128/79

OTHER PUBLICATIONS

Stanley–Surgery, vol. 68, No. 5, pp. 852–856.

Primary Examiner—Stephen C. Pellegrino
Attorney, Agent, or Firm—Quarles & Brady

[57] ABSTRACT

The penile implant of the present invention comprises a ring of soft biocompatible material which is adapted to be implanted beneath the skin of the penis of an incontinent male. The ring when implanted produces a protuberance which effectively increases the diameter of the penis so as to retain the flexible elastic sheath of a urinary collection device in place. A relatively stiff rod also may be implanted in the penis beneath the ring to support the ring. The protuberance produced by the implanted ring permits the patient to securely attach and easily remove the flexible sheath of the urinary collection device without the assistance of others.

4 Claims, 6 Drawing Figures

U.S. Patent     May 3, 1983     4,381,767
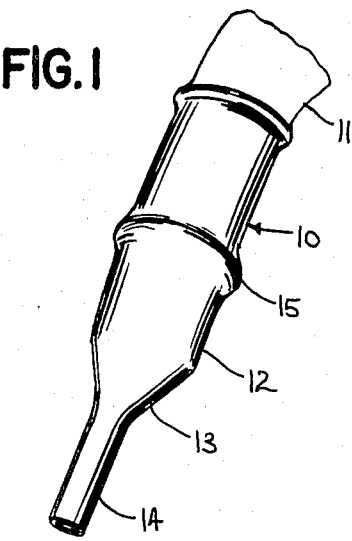
FIG.1
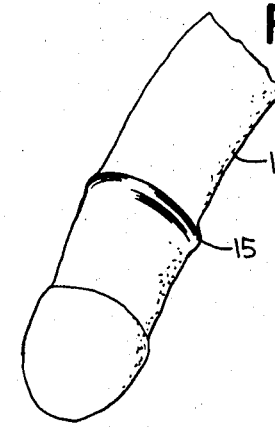
FIG.2
FIG.5
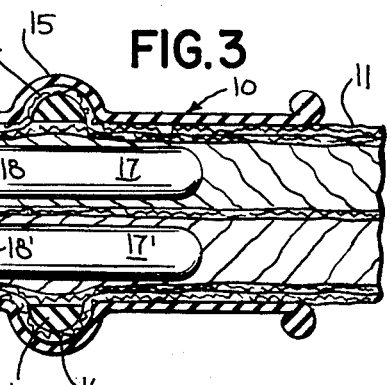
FIG.3
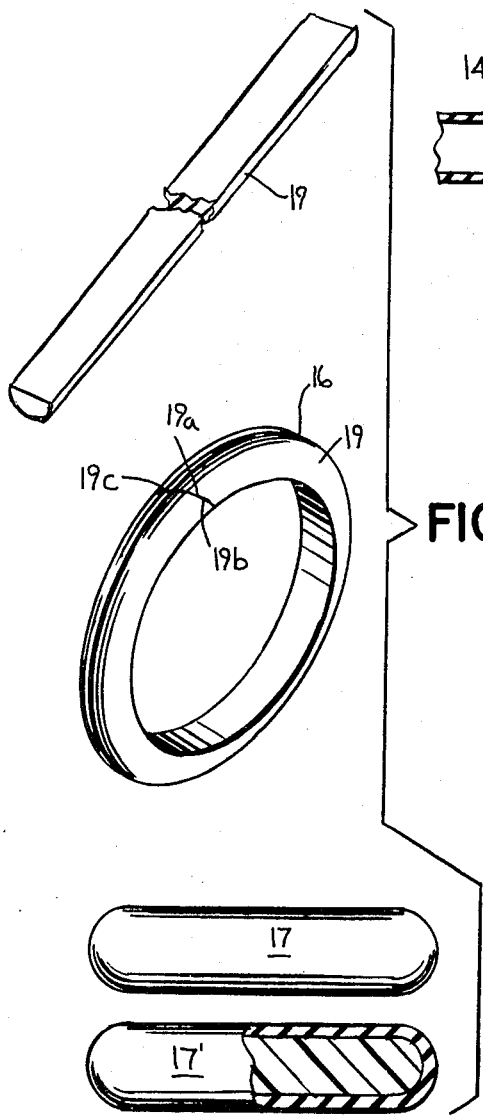
FIG.4
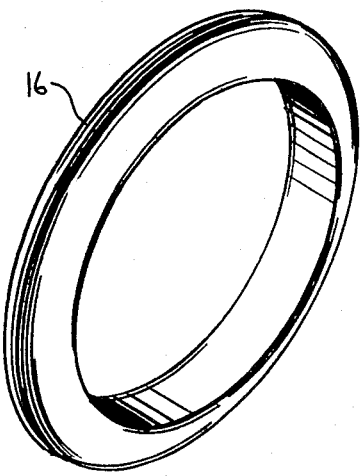
FIG.6

PENILE IMPLANT

The present invention relates to a penile implant and more particularly to a penile implant which is useful in retaining the flexible sheath of a urinal device in place on the penis of an incontinent male patient.

BACKGROUND OF THE INVENTION

Incontinent male patients, such as those suffering from spinal cord injuries, often wear devices for the collection of urine. The urinary collection device most widely used with incontinent male patients is commonly called a "Texas Catheter" and it consists of a flexible condom-like sheath which is secured to the patient's penis and a tubular member which connects the condom-like device to a suitable urine receptacle. A device of this type is shown in the Rogers et al U.S. Pat. No. 3,835,857, granted Sep. 17, 1974.

One of the problems involved in the use of the "Texas Catherter" is that the sheath which depends upon its elasticity to stay in place can be accidently removed quite easily from the patient's penis without the patient being aware of its removal. Another Rogers et al patent, U.S. Pat. No. 3,863,638, discloses a liner pad which has an adhesive coating which clings to the penis and which is designed to retain the elastic sheath on the penis. Still another patent relating to a sheath liner useful for this purpose is U.S. Pat. No. 4,187,851.

Although the use of an adhesive coated sheath liner is an improvement on the use of the sheath itself in preventing accidental removal, it is not without disadvantages. For example, the liner normally has to be either placed on or removed from the penis of the patient by a person other than the patient. In addition, the liner and its adhesive layer can cause tissue irritation. Obviously, therefore, a need still exists for an improved means or method for securely attaching the sheath of a Texas catheter to the penis of an incontinent male patient.

SUMMARY OF THE PRESENT INVENTION

It is an object of the present invention to disclose a novel method for retaining the sheath of a urinary collection device upon the penis of an incontinent male patient that does not require the use of liners.

It is another object of the present invention to disclose a penile implant which when surgically implanted provides a superior permanent means of retaining the flexible sheath of a urinary collection device in place.

The penile implant of the present invention is a ring of soft, flexible, biocompatible material which is implanted underneath the penile skin of the distal end of the patient's penis. The ring preferably is D-shaped in cross section and it is implanted with the curved belly of the D extending outwardly. The ring preferably is used in combination with at least one and generally two supportive rods of biocompatable material which also are implanted in the distal end of the penis. When two rods are used one is implanted in each of the corpus cavernosum of the penis. When a rod is used, the ring is implanted underneath the penile skin overlying the area in which the rod is implanted. The rod which is of a less soft or stiffer material than the ring serves to support the ring. The use of the rod makes it possible to use a softer material for the ring thereby minimizing the possibility of erosion of the ring through the penile skin.

These and still other objects and advantages of the invention will become apparent to those skilled in the art from the description and the drawings which follow.

BRIEF DESCRIPTION OF THE DRAWINGS

In the Drawing:

FIG. 1 is a perspective view of a penis with a ring of the present invention surgically implanted and a sheath of a urinary collection device in place;

FIG. 2 is a perspective view of a penis with the ring implanted therein but without the sheath;

FIG. 3 is a partial sectional top plan view taken along the line 3—3 in FIG. 1;

FIG. 4 is a perspective view, partly in section, of an elongated member of biocompatible material, a ring formed from the member and two rod implants;

FIG. 5 is a cross sectional view of the ring taken along line 5—5 in FIG. 4; and FIG. 6 is a perpective view of a second embodiment of the ring of the present invention.

DESCRIPTION OF THE PREFERRED EMBODIMENT

Referring to FIG. 1, a sheath 10 of a urinary collection device is shown in position upon a penis 11. The sheath 10 has a body portion 12 joined to a conical funnel like section 13 which terminates in a tube 14 which leads to a urine receptacle (not shown). The body portion 12 is of a very thin elastic material such as latex rubber which is capable of being rolled upon itself and then unrolled onto the penis 11 over a protuberance 15. Referring to FIG. 2, the penis 11 with the protuberance 15 is seen with the sheath 10 removed. As seen best in FIG. 3, the protuberance 15 is formed by a ring 16 implanted under the skin 11a of the penis 11.

Turning to FIG. 3 it can be seen that the penile implant includes both the ring 16 and a pair of rods 17,17', all of which are made of a physiologically inert material such as medical grade silicone rubber. The ring 16 is soft and flexible and it is implanted under the penile skin 11a above the corpora 11b of the penis 11 adjacent the distal end of the penis. The ring 16, as seen only in FIG. 5, is D-shaped in cross section. It is implanted as seen in FIG. 3 with the belly 16a of the D extending outwardly.

Referring to FIGS. 3 and 4, it is seen that each of the rods 17,17' is a relatively short cylinder with a paraboloidal tip 18 at each end which is shaped to conform to the inner shape of the distal end of the corpus cavernosum. The rods 17,17' are of a stiffer material than the ring 16 and each of the rods 17 and 17' is implanted in a separate corpus cavernosum 11b of the penis 11. If the patient is impotent, in place of the short rods 17,17', penile implants of the type disclosed in U.S. Pat. No. 4,066,037 may be used in place of the rods to support the ring 16 and to stiffen the penis for sexual intercourse.

In FIG. 4 an elongated, soft, flexible silicone member 19 of a D-shaped cross section is seen. The ring 16 seen in FIG. 4 is formed by trimming the member 19 to the desired length, mitering the ends 19a and 19b and forming the member 19 into a circle with the belly 16a of the D extending outwardly and securing the mitered ends 19a and 19b together to form a miter joint as at 19c in FIG. 4. The ends 19a and 19b may be secured together by use of a suitable adhesive or by other acceptable means.

Another embodiment of a ring 16 is seen in FIG. 6. As seen therein, the ring 16 is a molded seamless member which, of course, would have to be supplied in a variety of sizes.

Medical grade silicone rubber is the preferred material for the ring 16 and the rods 17,17' because it is biocompatible and it can be formulated to provide a material which possesses suitable tensile strength, stiffness and softness for the intended funcion. However, other materials possessing the desired properties also may be used.

The stiffness or softness of the material may be measured with a durometer, such as a Shore A durometer, which ascertains the depth of the penetration of a specified indentor into a specimen under specified conditions. A scale is chosen so that zero represents a material showing no measurable resistance to indentation and 100 represents a material showing no measurable indentation.

Tensile strength is the unit stress which produces failure of a specimen in tension. A Scott Tensile Tester may be used to measure the stress which produces failure.

In order to minimize the possibility of its erosion through the penil skin, the ring 16 is preferably formed of a material having a Shore A hardness of about 10 which is very soft and flexible and all edges are arced or curved. The rods 17,17' which provide support when needed for the ring 16 are of a relatively stiffer but still flexible material having a Shore A hardness of about 20. They are preferably covered with a layer of very soft silicone material. As previously mentioned, if the patient is impotent, a pair of composite penile rod implants of the type disclosed in U.S. Pat. No. 4,066,037 can be employed in place of the rods 17,17'.

While in the preferred embodiment two rods are implanted, in some instances the surgeon may prefer to use a single implanted rod such as the rod implant shown in the Geroux U.S. Pat. No. 3,991,752.

The preferred method of implantation of the ring 16 and the rods, 17,17' will now be described. After appropriate incisions, the corpora cavernosa are dilated distally to accept the rods 17,17'. The appropriate anatomical measurements are made to insure that the rods 17,17' will be properly positioned and one rod of appropriate size is inserted into the distal end of each of the corpus cavernosum with the tips 18,18' positioned in the tunica end of the respective corpus cavernosum.

The incisions are then closed, and the member 19 trimmed to size, the ends mitered and the ring 16 formed. The ring 16 is positioned about the corpora overlying the rods 17,17' but beneath the penile skin 11a. The ring 16, if desired, is then anchored in place with sutures and the incision in the penile skin closed.

It will be apparent to those skilled in the art that use of the ring implant of the present invention provides significant advantages over the previous methods of attaching the flexible elastic sheath of the urinary collection device to the penis. Prior art techniques are generally temporary and/or potentially unsanitary and/or require the assistance of others for proper placement of the sheath on the penis. In contrast, a patient with a ring implant of the present invention can simply and readily attach the condom-like sheath to his penis by himself by unrolling the prerolled sheath over the distal end of the penis and the protuberance formed by the implanted ring (as seen in FIG. 1). The protuberance formed by the implant increases the diameter of the penis and provides a very effective means of retaining the sheath in place.

It is to be understood that the foregoing description has been for purposes of illustration and that a number of modifications and changes may be made without departing from the spirit and scope of the present invention. For example, if desired one or more porous patches may be attached to the ring to permit tissue ingrowth to help anchor it in place. In addition, the ring, if it is to be used by itself, may be reinforced to make it self-supporting. Therefore, the invention is not to be limited by any of the specific embodiments described but only by the claims which follow:

I claim:

1. A method of modifying the penis of an incontinent male patient so that a flexible elastic sheath of a urinary collection device will be retained thereon which comprises surgically implanting underneath the penil skin a ring of biocompatible material having a Shore A hardness of about 10 to produce a protuberance which effectively increases the diameter of the penis so that the flexible elastic sheath of the urinary collection device is more securely retained.

2. The method of claim 1 in which at least one rod is implanted in the penis beneath the ring to provide support for the soft, flexible ring.

3. A kit for forming an implant which can be used to form a protuberance which can be used to more securely retain an elastic sheath of a urinary collection device on the penis of a patient, said kit comprising:
    (a) an elongated member of flexible, trimmable biocompatible material having a Shore A hardness of about 10, said member having a generally D-shaped cross sectional shape and being of at least sufficient length to encircle the patient's penis; and
    (b) means for securing the ends of said member together to form a ring.

4. The kit of claim 3 which includes at least one supportive implantable rod.

* * * * *